(12) United States Patent
Dreyfuss et al.

(10) Patent No.: US 9,622,738 B2
(45) Date of Patent: Apr. 18, 2017

(54) SOFT ANCHOR ASSEMBLY WITH NON-SLIDING FLEXIBLE STRAND AND TECHNIQUES FOR USE

(71) Applicant: ARTHREX, INC., Naples, FL (US)

(72) Inventors: Peter Dreyfuss, Naples, FL (US); John Sodeika, Naples, FL (US); Laurence Higgins, Brookline, MA (US)

(73) Assignee: Arthrex, Inc., Naples, FL (US)

( * ) Notice: Subject to any disclaimer, the term of this patent is extended or adjusted under 35 U.S.C. 154(b) by 218 days.

(21) Appl. No.: 14/483,261

(22) Filed: Sep. 11, 2014

(65) Prior Publication Data

US 2016/0074030 A1 Mar. 17, 2016

(51) Int. Cl.
*A61B 17/04* (2006.01)
*A61F 2/08* (2006.01)
*A61B 17/06* (2006.01)

(52) U.S. Cl.
CPC ........ *A61B 17/0401* (2013.01); *A61F 2/0811* (2013.01); *A61B 17/0466* (2013.01); *A61B 2017/042* (2013.01); *A61B 2017/0403* (2013.01); *A61B 2017/0406* (2013.01); *A61B 2017/0414* (2013.01); *A61B 2017/0448* (2013.01); *A61B 2017/0464* (2013.01); *A61B 2017/06185* (2013.01); *A61F 2002/0817* (2013.01)

(58) Field of Classification Search
CPC ............ A61B 17/0401; A61B 17/0466; A61B 2017/0409; A61B 2017/0414; A61B 2017/042; A61B 2017/0464; A61B 2017/0448; A61B 2017/0403; A61B 2017/0406; A61B 2017/06185; A61F 2/0811; A61F 2002/0847; A61F 2002/0852; A61F 2002/0817
See application file for complete search history.

(56) References Cited

U.S. PATENT DOCUMENTS

| | | | |
|---|---|---|---|
| 5,989,252 A | 11/1999 | Fumex | |
| 6,511,498 B1 | 1/2003 | Fumex | |
| 7,749,250 B2 | 7/2010 | Stone et al. | |
| 8,273,106 B2 | 9/2012 | Stone et al. | |
| 8,562,647 B2 | 10/2013 | Kaiser et al. | |
| 2005/0192631 A1* | 9/2005 | Grafton | A61B 17/06166 606/228 |
| 2007/0055206 A1* | 3/2007 | To | A61B 17/0401 604/191 |
| 2008/0065114 A1* | 3/2008 | Stone | A61B 17/0401 606/139 |
| 2009/0318960 A1 | 12/2009 | Burkhart | |

(Continued)

FOREIGN PATENT DOCUMENTS

| | | |
|---|---|---|
| WO | 2014151766 | 9/2014 |
| WO | 2015095534 | 6/2015 |

OTHER PUBLICATIONS

Extended European Search Report for European Application No. 15182593.2, mailed Feb. 5, 2016.

*Primary Examiner* — Jocelin Tanner
(74) *Attorney, Agent, or Firm* — Blank Rome LLP

(57) ABSTRACT

A soft anchor assembly according to an exemplary aspect of the present disclosure includes, among other things, a sheath, a first flexible strand affixed as non-sliding relative to the sheath and a second flexible strand slidable relative to the sheath.

13 Claims, 7 Drawing Sheets

(56) References Cited

U.S. PATENT DOCUMENTS

| | | |
|---|---|---|
| 2009/0318961 A1* | 12/2009 | Stone ................ A61B 17/0401 606/228 |
| 2012/0197271 A1 | 8/2012 | Astorino et al. |
| 2012/0253365 A1* | 10/2012 | Sikora ................ A61B 17/0401 606/148 |
| 2012/0290004 A1 | 11/2012 | Lomardo et al. |
| 2013/0116730 A1* | 5/2013 | Denham ............ A61B 17/0401 606/232 |
| 2013/0123810 A1 | 5/2013 | Brown et al. |
| 2013/0296936 A1 | 11/2013 | Burkhart |
| 2014/0046368 A1 | 2/2014 | Kaiser et al. |
| 2014/0052178 A1 | 2/2014 | Dooney, Jr. |
| 2014/0052179 A1 | 2/2014 | Dreyfuss et al. |

* cited by examiner

SOFT ANCHOR ASSEMBLY WITH NON-SLIDING FLEXIBLE STRAND AND TECHNIQUES FOR USE

BACKGROUND

This disclosure relates to a surgical device and methods of using the surgical device to attach tissue to bone. More particularly, this disclosure is directed to a soft anchor assembly that includes a sheath and a flexible strand affixed as non-sliding relative to the sheath.

Orthopedic procedures are often performed to repair musculoskeletal injuries. For example, soft tissue may tear away from bone during vigorous exercise or sporting activities. When such tears occur, reattachment is often necessary to repair the damaged tissue. Suture anchors are one type of surgical device that has been developed to facilitate these repairs.

Rotator cuff tears are one common condition causing shoulder disability in patients. Failure of the rotator cuff tendon may result in pain in the shoulder and/or loss of shoulder function. Several different arthroscopic repair techniques are known for repairing rotor cuff tears, including single-row, double-row and bridging techniques. Additional advancements in this field of technology are desired.

SUMMARY

A soft anchor assembly according to an exemplary aspect of the present disclosure includes, among other things, a sheath, a first flexible strand affixed as non-sliding relative to the sheath and a second flexible strand slidable relative to the sheath.

In a further non-limiting embodiment of the foregoing assembly, the sheath is a tubular sleeve made of a flexible suture material.

In a further non-limiting embodiment of either of the foregoing assemblies, the first flexible strand and the second flexible strand are both passed through portions of a bore that extends through the sheath.

In a further non-limiting embodiment of any of the foregoing assemblies, the first flexible strand exits the sheath at a different location from the second flexible strand.

In a further non-limiting embodiment of any of the foregoing assemblies, the first flexible strand is a suture tape and the second flexible strand is a suture.

In a further non-limiting embodiment of any of the foregoing assemblies, the first flexible strand is a suture tape or a suture and the second flexible strand is a suture.

In a further non-limiting embodiment of any of the foregoing assemblies, at least one stitch fixates the first flexible strand to the sheath.

In a further non-limiting embodiment of any of the foregoing assemblies, a first portion of the first flexible strand exits the sheath through a first opening and a second portion of the first flexible strand exits the sheath through a second opening.

In a further non-limiting embodiment of any of the foregoing assemblies, the second flexible strand exits the sheath at least at two locations that are between the first opening and the second opening.

In a further non-limiting embodiment of any of the foregoing assemblies, the first portion of the first flexible strand is affixed to the sheath with a first stitch and the second portion of the first flexible strand is affixed to the sheath with a second stitch.

A method according to another exemplary aspect of the present disclosure includes, among other things, attaching tissue to a bone, the attaching step including the use of a soft anchor assembly that includes a sheath and a first flexible strand fixated as non-sliding to the sheath.

In a further non-limiting embodiment of the foregoing method, the attaching step includes inserting the soft anchor assembly into the bone, inserting a knotless anchor into the bone laterally from the soft anchor assembly and connecting the first flexible strand of the soft anchor assembly to the knotless anchor.

In a further non-limiting embodiment of either of the foregoing methods, the inserting step includes inserting the soft anchor assembly through the tissue as part of a trans-tendon technique.

In a further non-limiting embodiment of any of the foregoing methods, the connecting step includes loading a free end of the first flexible strand through an eyelet of the knotless anchor.

In a further non-limiting embodiment of any of the foregoing methods, the method includes tensioning the tissue by pulling on the first flexible strand.

In a further non-limiting embodiment of any of the foregoing methods, the soft anchor assembly includes a second flexible strand, and the attaching step includes tying a knot in the second flexible strand.

A method of attaching tissue to bone according to another exemplary aspect of the present disclosure includes, among other things, inserting a first medial row of fixation devices into a bone, the first medial row of fixation devices including at least one soft anchor assembly that includes a sheath and a first flexible strand fixated as non-sliding relative to the sheath. The method includes inserting a second lateral row of fixation devices into the bone, the second lateral row of fixation devices including at least one knotless anchor and connecting the first flexible strand of the at least one soft anchor assembly to the at least one knotless anchor.

In a further non-limiting embodiment of the foregoing method, the at least one soft anchor assembly is inserted through a tissue and into the bone.

In a further non-limiting embodiment of either of the foregoing methods, the at least one soft anchor assembly includes a second flexible strand that is slidable relative to the sheath, and comprising tying a knot in the second flexible strand to attach a tissue to the bone.

In a further non-limiting embodiment of any of the foregoing methods, the connecting step includes loading a free end of the first flexible strand through a portion of the at least one knotless anchor, tensioning the free end of the first flexible strand to achieve a desired tension on a tissue and inserting the at least one knotless anchor into the bone.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes various soft anchor assemblies and associated surgical techniques for attaching tissue to bone. The soft anchor assemblies are formed of "soft" materials, such as suture materials, that confer the ability to be inserted into bone sockets/holes and bunch together, collapse, expand and/or change shape to fixate within the socket/hole. In some embodiments, the soft anchor assembly includes a sheath and a flexible strand affixed as non-sliding relative to the sheath. In other embodiments, the soft anchor assembly includes a sheath, a first flexible strand affixed as non-sliding to the sheath, and a second flexible strand that is slideable relative to the sheath. The soft anchor assemblies of this disclosure may be utilized in various surgical techniques to attach tissue to bone. These and other features are described in greater detail in the paragraphs that follow.

Figure 1A:
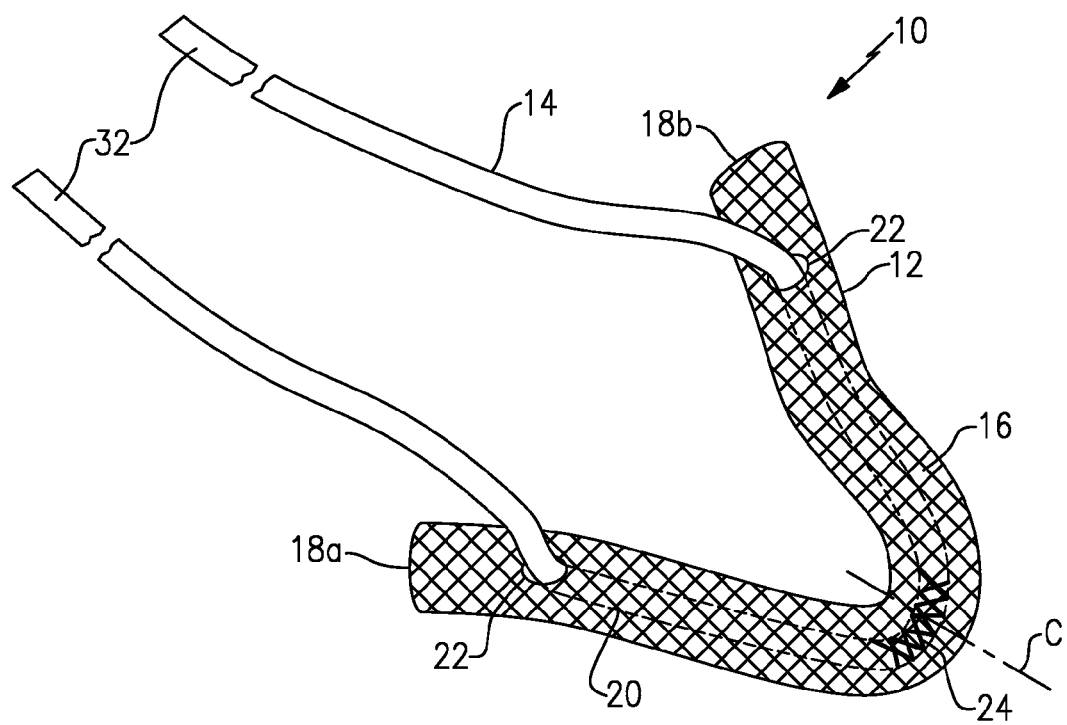
FIGS. 1A and 1B illustrate a soft anchor assembly according to a first embodiment of this disclosure.
Figure 1B:
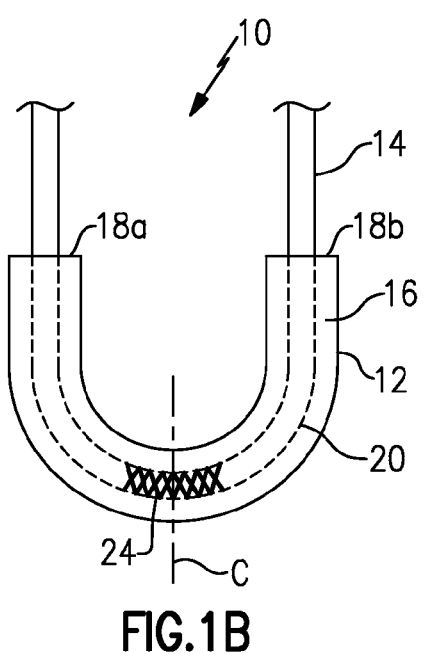

FIGS. 1A and 1B illustrate a soft anchor assembly 10. The soft anchor assembly 10 is configured for use in various soft tissue repairs or fixations and may be fixated inside bone for attaching tissue (e.g., ligament, tendon, graft, etc.) to bone. For example, the soft anchor assembly 10 can be used in conjunction with a variety of orthopedic surgical repairs, including but not limited to rotator cuff repairs, Achilles tendon repairs, patellar tendon repairs, ACL/PCL reconstructions, hip and shoulder reconstructions, among many others.

In this disclosure, the soft anchor assembly 10 is referred to as a "soft" construct because it is formed of soft materials such as yarns, fibers, filaments, strings, fibrils, strands, sutures, etc., or any combination of such materials. The soft materials may be synthetic or natural materials, or combinations of synthetic and natural materials, and may be bio-degradable or non-degradable within the scope of this disclosure. In one non-limiting embodiment, the soft anchor assembly 10 is made exclusively of soft, suture-based materials.

The exemplary soft anchor assembly 10 may include a sheath 12 and a flexible strand 14 that is affixed as non-sliding relative to the sheath 12. The sheath 12 includes a tubular body 16 that extends between opposing ends 18a, 18b. The opposing ends 18a, 18b may be open or closed ends. The tubular body 16 establishes a bore 20 that extends between the opposing ends 18a, 18b.

In one embodiment, the sheath 12 is a tubular sleeve made of a flexible material, such as a braided, woven, or knitted structure made of yarns, fibers, filaments, sutures or similar materials, or combinations of these materials. In one non-limiting embodiment, the sheath 12 is constructed of polyester suture material. Other materials may also be suitable to construct the sheath 12.

The flexible strand 14 is passed through at least a portion of the bore 20 of the sheath 12. The flexible strand 14 may assist in bunching together the sheath 12 once the soft anchor assembly 10 is inserted into bone and the flexible strand 14 is tensioned. In one embodiment, the flexible strand 14 passes through openings 22 formed through the tubular body 16 and which are spaced from the opposing ends 18a, 18b of the sheath 12 (see FIG. 1A). The flexible strand 14 may be of any length and includes free ends 32 that extend outside of the sheath 12. This configuration can be used if the opposing ends 18a, 18b are closed ends. The flexible strand 14 could alternatively pass directly through the opposing ends 18a, 18b if the opposing ends 18a, 18b are configured as open ends (see FIG. 1B).

In one embodiment, the flexible strand 14 is a suture. Non-limiting examples of suitable sutures include FiberWire®, TigerWire®, or FiberChain® suture, although any type of suture may be utilized, including cored or coreless sutures. In another embodiment, the flexible strand 14 is suture tape, such as FiberTape®. The flexible strand 14 could include any soft, flexible strand of material.

The flexible strand 14 is affixed as non-sliding relative to the sheath 12. In other words, the flexible strand 14 is not slidable inside the bore 20 to change its positioning relative to the sheath 12. Fixating the flexible strand 14 to the sheath 12 improves the ability to tension the flexible strand 14, such as during bridging techniques, as is further discussed below.

In one embodiment, the flexible strand 14 is affixed to the sheath 12 by a stitch 24. The stitch 24 may extend through both the sheath 12 and the flexible strand 14 to fixate the flexible strand 14 to the sheath 12. Alternatively, the flexible strand 14 could be glued or bonded to the sheath 12. Other fixating techniques may also be utilized. In one embodiment, the stitch 24 is provided near a center C of the sheath 12.

Figure 2:
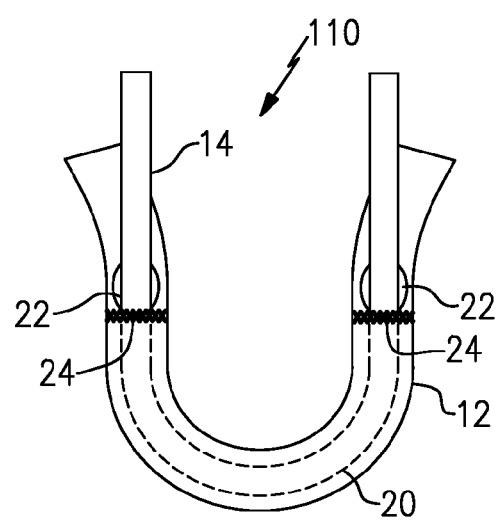
FIG. 2 illustrates a soft anchor assembly according to a second embodiment of this disclosure.

FIG. 2 illustrates another soft anchor assembly 110. In this disclosure like reference numerals designate like elements where appropriate and reference numerals with the addition of 100 or multiples thereof designate modified elements that are understood to incorporate the same features and benefits of the corresponding original elements.

The soft anchor assembly 110 of FIG. 2 is similar to the soft anchor assembly 10 of FIG. 1. However, in this embodiment, the flexible strand 14 is affixed to the sheath 12 at multiple locations using multiple stitches 24. In one embodiment, stitches 24 are provided near each opening 22 through which the flexible strand 14 passes through the sheath 12. Although two stitches 24 are shown in FIG. 2, the soft anchor assembly 110 could include any number of stitches for configuring the flexible strand 14 as non-sliding relative to the sheath 12.

FIGS. 3A-3F schematically illustrate an exemplary method for attaching tissue to bone using one or more soft anchor assemblies. Either of the soft anchor assemblies 10, 110 can be utilized to attach tissue to bone. The soft anchor assemblies 10, 110 can be utilized in single-row techniques, double-row techniques, or any bridging technique to attach tissue to bone. In this non-limiting embodiment, the method is used to repair a torn rotator cuff. However, other repairs are also contemplated.

Figure 3A:
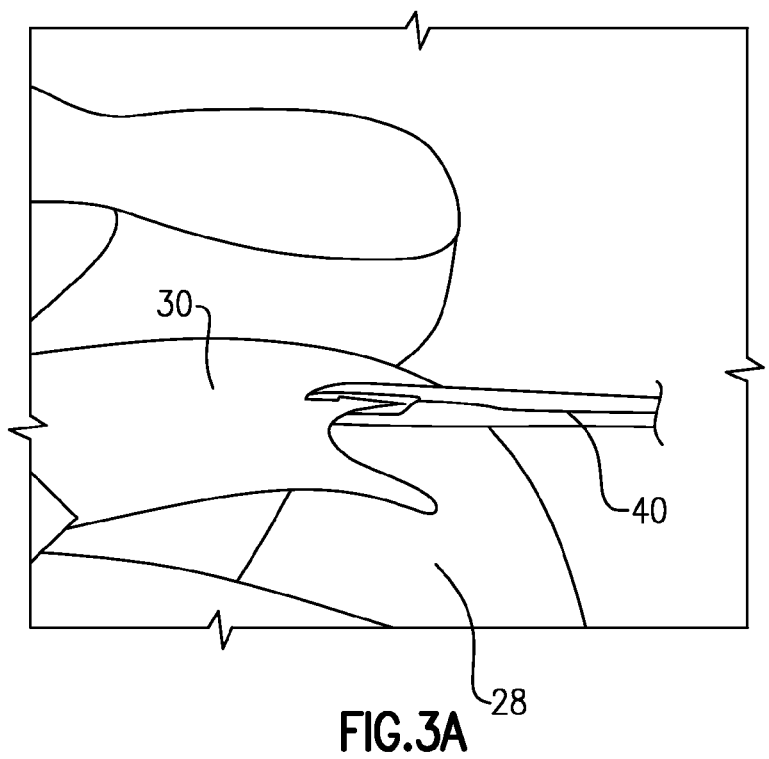
FIGS. 3A, 3B, 3C, 3D, 3E and 3F illustrate a method of attaching tissue to bone using a soft anchor assembly.

First, as shown in FIG. 3A, the size and mobility of a torn tissue 30 is assessed using a tool 40, such as tissue grasper. One suitable tissue grasper is Arthrex's KingFisher® suture retriever/tissue grasper. A bleeding bed may be created adjacent to the tissue 30 to enhance healing of the tissue 30 to bone 28. In one non-limiting embodiment, the tissue 30 is a rotor cuff and the bone 28 is a humerus.

Figure 3B:
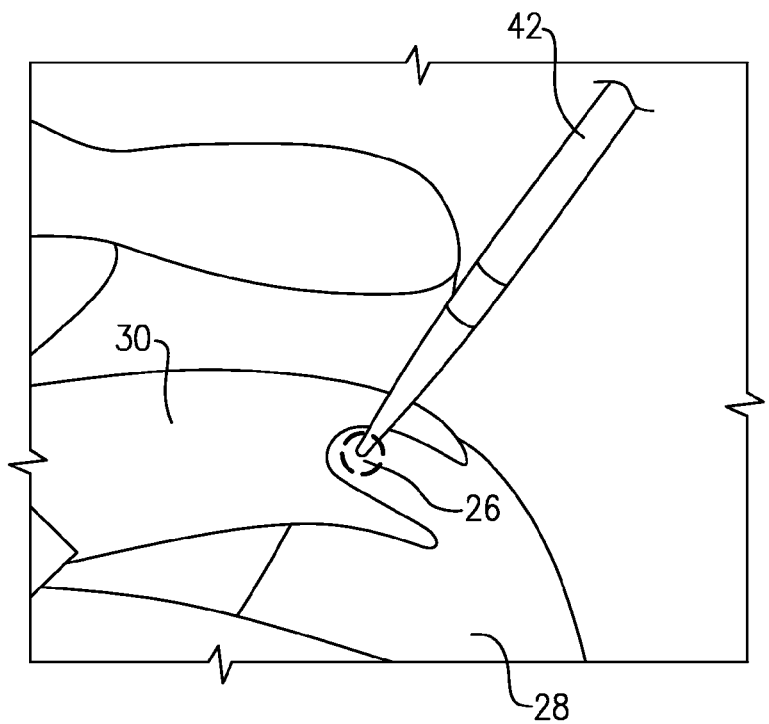
Figure 3C:
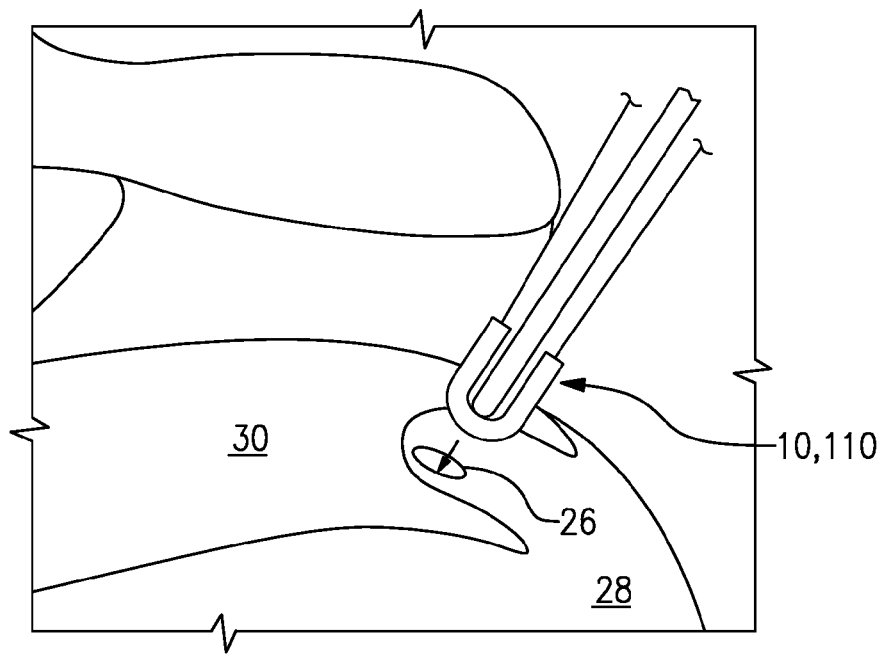

Next, the bone 28 is prepared for receiving a medial row of fixation devices. The medial row of fixation devices may include one or more soft anchor assemblies 10, 110, in one non-limiting embodiment. Referring to FIGS. 3B and 3C, bone sockets 26 are prepared using a tool 42, such as a punch, adjacent to the articular margin of the bone 28. In one embodiment, the bone sockets 26 are formed at a 45° "deadman" angle.

Figure 3D:
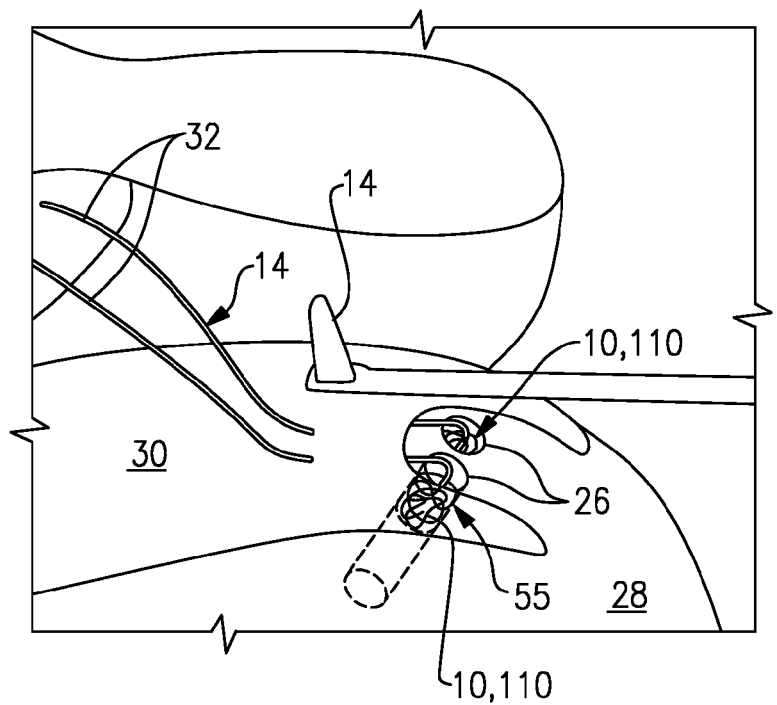

The soft anchor assemblies 10, 110 are then inserted into the bone sockets 26 (see FIG. 3C). The soft anchor assemblies 10, 110 bunch together to form an anchoring cluster 55 within the bone sockets 26 (see FIG. 3D). The bunched together anchoring cluster 55 promotes fixation of the soft anchor assemblies 10, 110 within the bone sockets 26. As shown in FIG. 3D, free ends 32 of the flexible strand 14 of each suture anchor assembly 10, 110 of the medial row may next be passed through the tissue 30.

The bone 28 is next prepared for insertion of a lateral row of fixation devices. The lateral row of fixation devices may include one or more knotless anchors. In one non-limiting embodiment, the knotless anchors include SwivelLock® anchors. In another embodiment, the knotless anchors include PushLock® anchors. However, other knotless anchors may also be utilized.

Figure 3E:
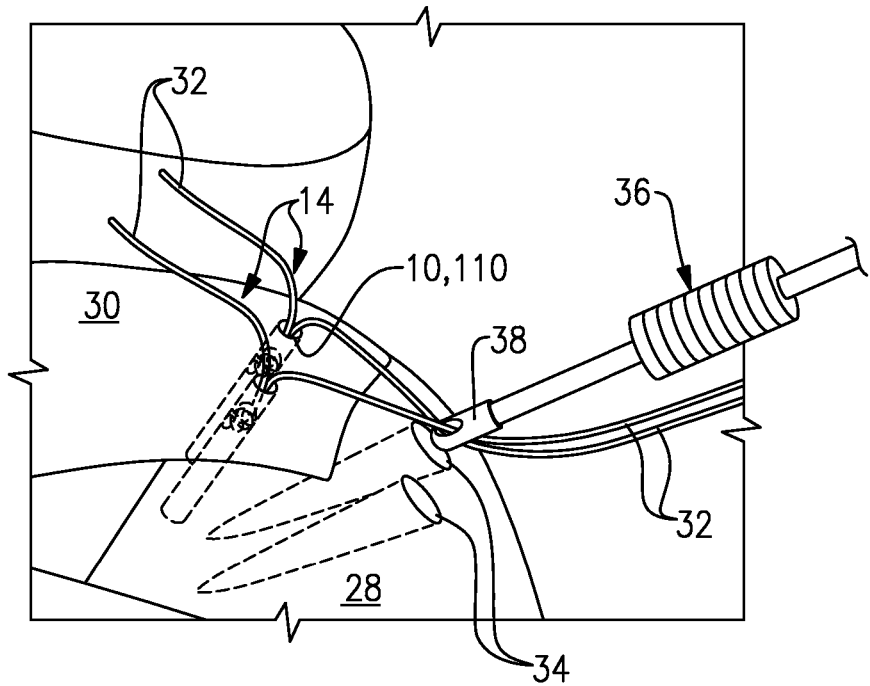

As shown in FIG. 3E, additional bone sockets 34 are prepared for insertion of the knotless anchors 36 into the bone 28. The bone sockets 34 may be prepared laterally from the medial row of anchors and slightly distal to the greater tuberosity of the bone 28. One free end 32 from the flexible strand 14 of each soft anchor assembly 10, 110 of the medial row may be connected to each knotless anchor 36 of the lateral row. For example, in one embodiment, the free ends 32 are loaded through a portion 38, such as an eyelet, of each knotless anchor 36.

Tension may be applied to the flexible strands 14 so that the tissue 30 is reduced and compressed against the bone 28, and once a desired tissue tension is achieved, the knotless anchors 36 are inserted into the bone sockets 34 to complete the repair. Because the flexible strands 14 are fixated as non-sliding relative to the sheath 12 of each soft anchor assembly 10, 110, each free end 32 of each flexible strand 14 may be tensioned individually and prior to insertion of the final fixation device of the lateral row. Stated another way, use of the soft anchor assemblies 10, 110 avoids the necessity of achieving tensioning with a single anchor of the lateral row.

Insertion in the manner described above configures the flexible strands 14 in a crisscross pattern P (see FIG. 3F) that provides a desired area of footprint compression. Any crisscross pattern using any number of fixations devices and flexible strands can be achieved by using the soft anchor assemblies 10, 110 in a bridging technique.

Figure 4A:
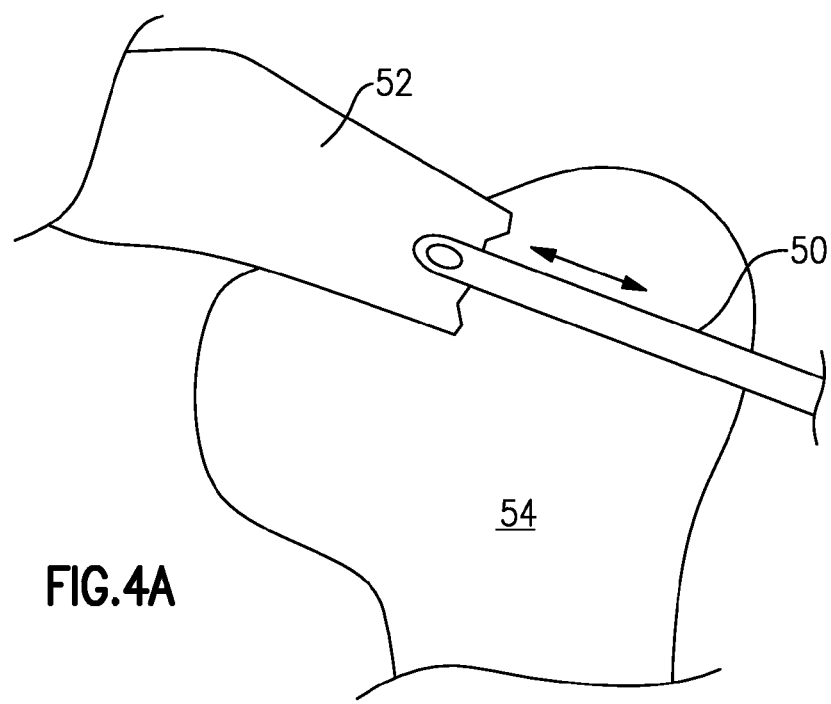
FIGS. 4A and 4B illustrate portions of another method of attaching soft tissue to bone using a soft anchor assembly.
Figure 4B:
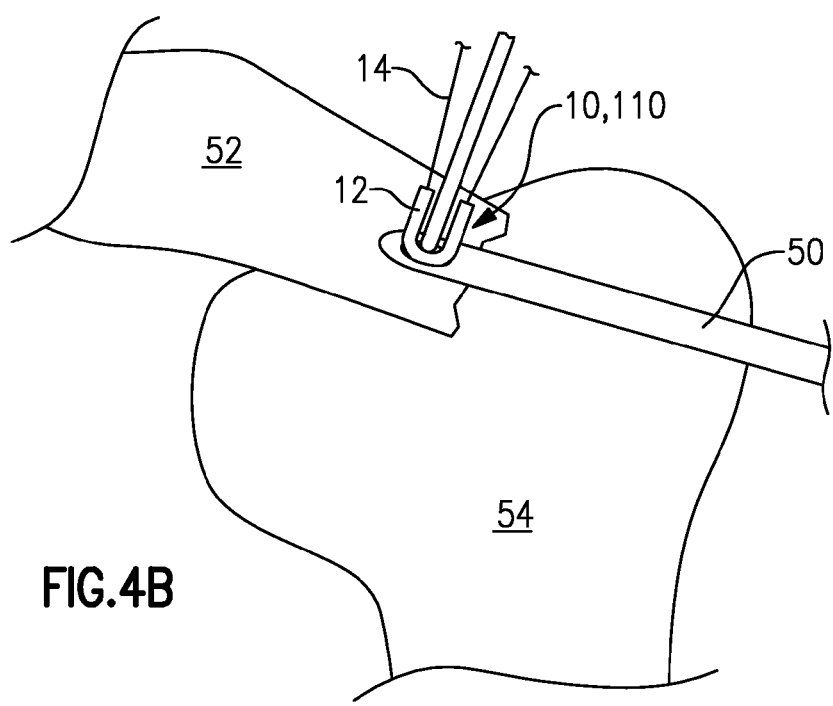

FIGS. 4A and 4B illustrate another method of attaching tissue to bone using one or more soft anchor assemblies 10, 110. In this embodiment, the method is a trans-tendon bridging technique.

Referring first to FIG. 4A, a tool 50 is used to grasp and mobilize a torn tissue 52 to a desired spot relative to an associated bone 54. If the tissue 52 is a rotor cuff, a surgeon would position the tissue 52 near the articular margin of the humerus bone.

Figure 3F:
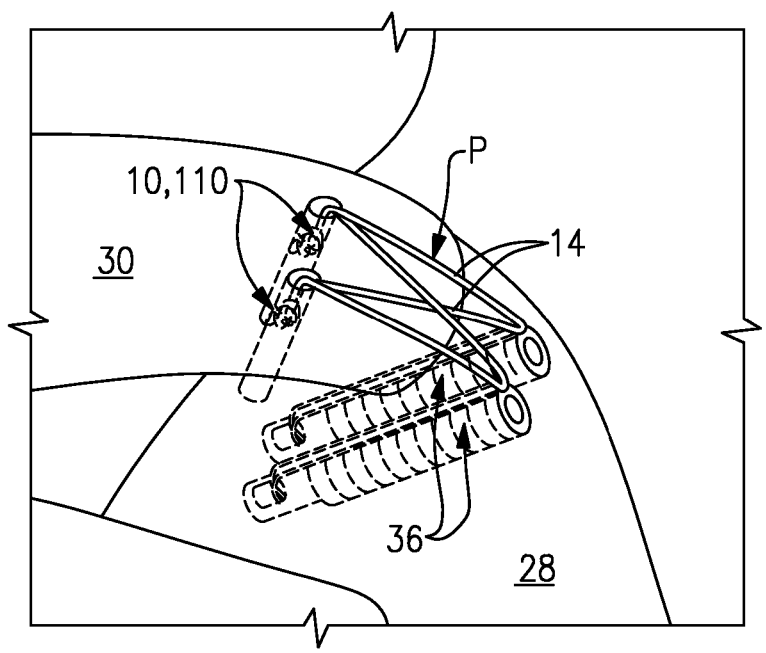

Next, as shown in FIG. 4B, while maintaining the desired tension on the tissue 52, a soft anchor assembly 10, 110 that includes a sheath 12 and a flexible stand 14 affixed as non-sliding relative to the sheath 12 is inserted directly through the tissue 52 and into the bone 54. In one embodiment, the soft anchor assembly 10, 110 is inserted through the tool 50 and then through the tissue 52. Bone sockets may be prepared in the bone 54 prior to inserting the soft anchor assembly 10, 110. Additional soft anchor assemblies 10, 110 may next be inserted in a similar manner to position a medial row of fixation devices. The trans-tendon technique may then proceed in a similar manner as shown in FIGS. 3E and 3F to insert a lateral row of fixation devices and complete the bridging repair.

Figure 5A:
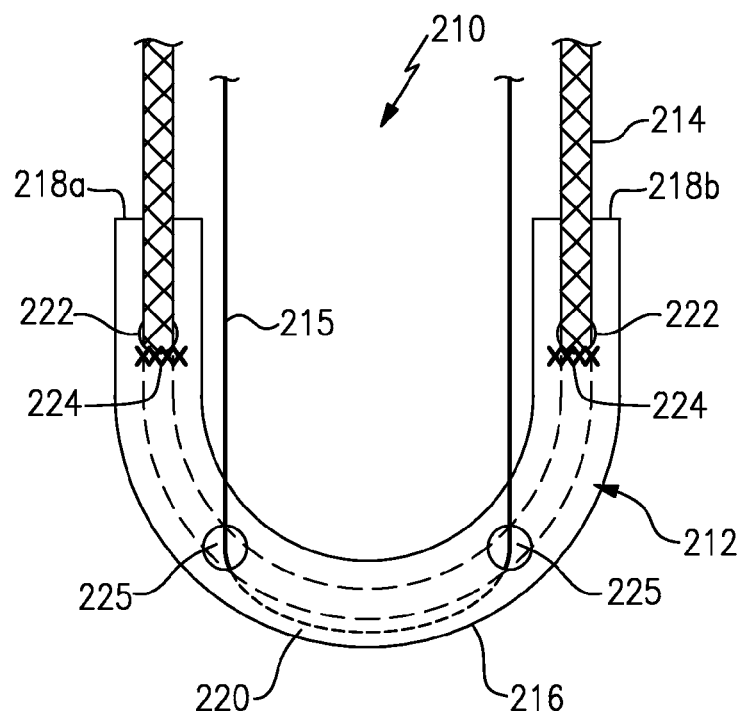
FIGS. 5A and 5B illustrate a soft anchor assembly according to another embodiment of this disclosure.
Figure 5B:
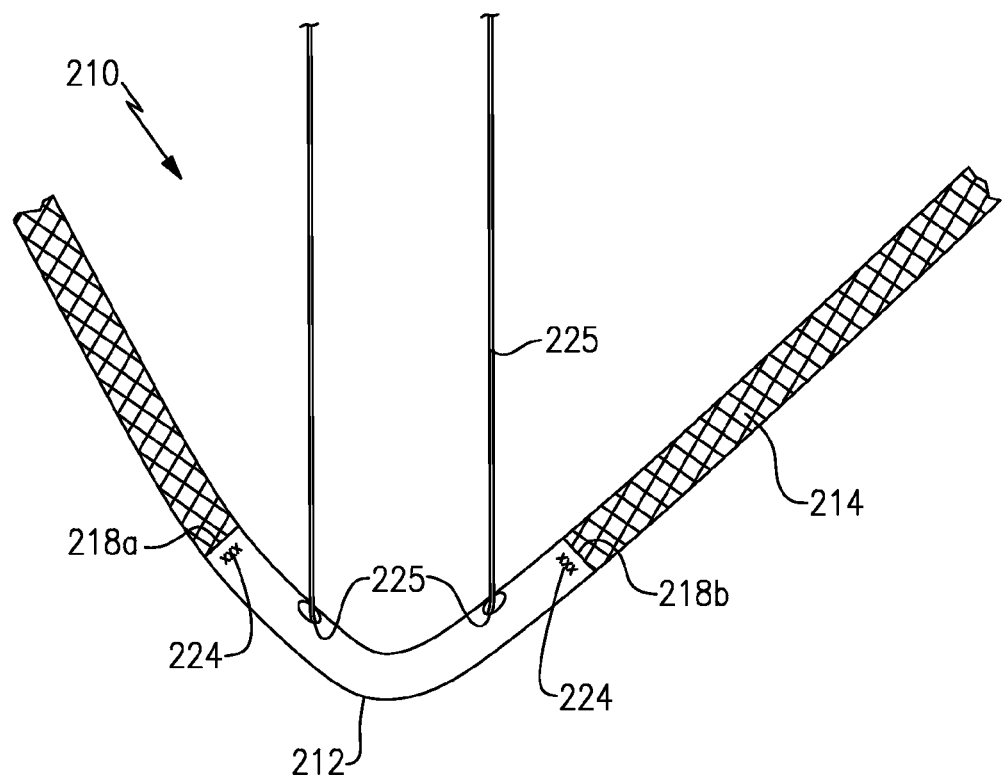

FIGS. 5A and 5B illustrate another soft anchor assembly 210 that can be utilized in various soft tissue repairs and fixations. The soft anchor assembly 210 includes a sheath 212 and a first flexible strand 214 that is affixed as non-sliding relative to the sheath 212. One or more stitches 224 are used to fixate the first flexible strand 214 relative to the sheath 212. The sheath 212 includes a tubular body 216 that extends between opposing ends 218a, 218b. The tubular body 216 establishes a bore 220 that extends between the opposing ends 218a, 218b. The first flexible strand 214 is at least partially accommodated inside the bore 220.

The soft anchor assembly 210 may additionally include a second flexible strand 215. The second flexible strand 215 may slide relative to the sheath 212. The bore 220 is sized such that it can accommodate both the first flexible strand 214 and the second flexible strand 215.

In one embodiment, the first flexible strand 214 is a suture tape and the second flexible strand 215 is a suture. In another embodiment, the first flexible strand 214 and the second flexible stand 215 are both sutures.

The first flexible strand 214 and the second flexible strand 215 may exit the sheath 212 at different locations. For example, in one embodiment, the first flexible strand 214 exits the sheath 212 through openings 222 formed through the tubular body 216 that are spaced from the opposing ends 218a, 218b, whereas the second flexible strand 215 passes through openings 225 that are intermediate of the openings 222 (see FIG. 5A). In another embodiment, the first flexible strand 214 passes directly through the opposing ends 218a, 218b, and the second flexible strand 215 exits the sheath 212 through openings 225 that are positioned between the opposing ends 218a, 218b (see FIG. 5B).

Figure 6:
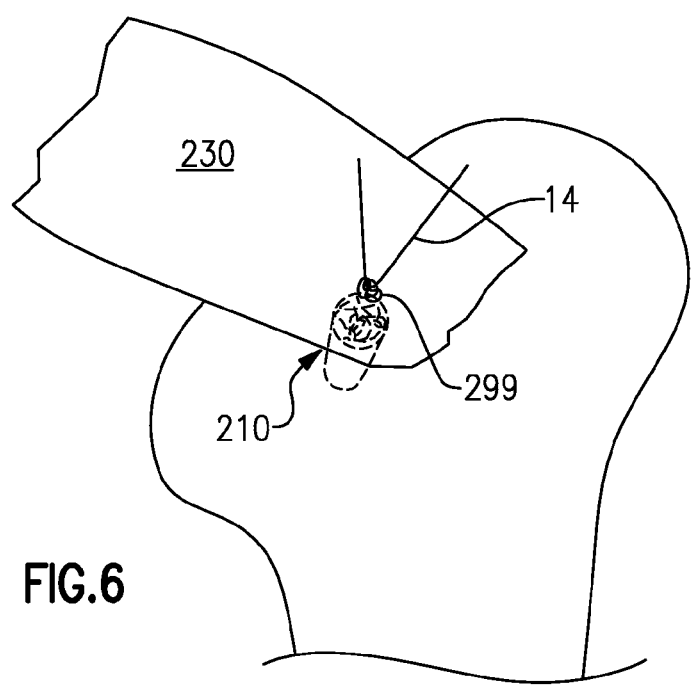
FIG. 6 illustrates one non-limiting use of the soft anchor assembly of FIGS. 5A and 5B.

The soft anchor assembly 210 can be used in a variety of techniques to attach tissue to bone. In one embodiment, the soft anchor assembly 210 may be employed in techniques similar to those shown in FIG. 3A-3F or 4A-4B. However, in addition to the steps shown in those exemplary techniques, the second flexible strand 215 can be used to tie knots 299 in the medial row on top of a tissue 230 (see, for example, FIG. 6). If knots are not desired, the second flexible strand 215 is simply removed from the soft anchor assembly 210 during the repair. In this way, the soft anchor assembly 210 can be employed as either a knotted or a knotless construct.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A soft anchor assembly, comprising:
a sheath having a bore between opposing ends;
a first flexible strand received in a portion of said bore, said first flexible strand being affixed to said sheath so as to be non-sliding relative to said sheath, and a first portion of said first flexible strand exits said sheath through a first opening and a second portion of said first flexible strand exits said sheath through a second opening; and
a second flexible strand slidable relative to said sheath and received in said portion of said bore of said sheath.

2. The assembly as recited in claim 1, wherein said sheath is a tubular sleeve made of a flexible suture material.

3. The assembly as recited in claim 1, wherein said first flexible strand exits said sheath at a different location from said second flexible strand.

4. The assembly as recited in claim 1, wherein said first flexible strand is a suture tape and said second flexible strand is a suture.

5. The assembly as recited in claim 1, comprising at least one stitch that fixates said first flexible strand to said sheath.

6. The assembly as recited in claim 1, wherein said second flexible strand exits said sheath at least at two locations that are between said first opening and said second opening.

7. The assembly as recited in claim 1, wherein said first portion of said first flexible strand is affixed to said sheath with a first stitch and said second portion of said first flexible strand is affixed to said sheath with a second stitch.

8. The assembly as recited in claim 1, wherein said first flexible strand includes opposing free ends and said second flexible strand includes opposing free ends, and said bore of said sheath receiving a portion of said first and second flexible strands between said opposing free ends of said first and second flexible strands, respectively.

9. The assembly as recited in claim 1, wherein said first flexible strand is affixed to a center of said sheath.

10. The assembly as recited in claim 1, wherein said first flexible strand is affixed to said sheath at multiple locations.

11. The assembly as recited in claim 1, wherein said second flexible strand includes opposing free ends, and said free ends are tied in a knot.

12. The assembly as recited in claim 1, wherein said first flexible strand includes opposing free ends, and said free ends extend through openings, respectively, at said opposing ends of said bore of said sheath.

13. A soft anchor assembly, comprising:
a sheath having a bore between opposing ends and an opening at each end, respectively;
a first flexible strand received in a portion of said bore, said first flexible strand includes opposing free ends, said free ends extending through said openings, respectively, at said opposing ends of said bore of said sheath, said first flexible strand being affixed to said sheath so as to be non-sliding relative to said sheath; and
a second flexible strand slidable relative to said sheath and received in said portion of said bore of said sheath.

* * * * *